(12) United States Patent
Neeff et al.

(10) Patent No.: US 7,714,144 B2
(45) Date of Patent: May 11, 2010

(54) METHOD FOR THE PRODUCTION OF 5-FLUORO-1,3-DIALKYL-1H-PYRAZOL-4-CARBONYL FLUORIDES

(75) Inventors: Arnd Neeff, Ennepetal (DE); Sergiy Pazenok, Solingen (DE)

(73) Assignee: Bayer CropScience AG, Monheim (DE)

( * ) Notice: Subject to any disclaimer, the term of this patent is extended or adjusted under 35 U.S.C. 154(b) by 102 days.

(21) Appl. No.: 12/066,377

(22) PCT Filed: Sep. 5, 2006

(86) PCT No.: PCT/EP2006/008635

§ 371 (c)(1),
(2), (4) Date: Aug. 15, 2008

(87) PCT Pub. No.: WO2007/031212

PCT Pub. Date: Mar. 22, 2007

(65) Prior Publication Data

US 2009/0306401 A1 Dec. 10, 2009

(30) Foreign Application Priority Data

Sep. 17, 2005 (DE) ........................ 10 2005 044 451

(51) Int. Cl.
*C07D 231/10* (2006.01)
(52) U.S. Cl. .................................................. 548/374.1
(58) Field of Classification Search ................ 548/374.1
See application file for complete search history.

(56) References Cited

U.S. PATENT DOCUMENTS 5,082,968 A    1/1992  Brunelle 5,675,016 A * 10/1997  Gallenkamp et al. ..... 548/374.1

FOREIGN PATENT DOCUMENTS

| EP | 0776889 | 6/1997 |
| EP | 1266904 | 12/2002 |
| JP | 04026651 | 1/1992 |
| WO | 98/32532 | 7/1998 |

OTHER PUBLICATIONS

International Search Report of PCT/EP2006/008635, completed Feb. 7, 2007.
Pleschke et al., "Halex reactions of aromatic compounds catalysed by 2-azaallenium, carbophosphazenium, aminophonium and diphosphazenium salts: a comparative study", Journal of Fluorine Chemistry, 2004, XP004586028.
Database WPI Week 1992, Derwent Publications Ltd., London, GB, XP002418846.
Database WPI Week 1988, Derwent Publications Ltd., London, GB, XP002418742.
Banks et al., "Halex fluorination of chlorinated benzaldehydes and benzoylchlorides", Journal of Fluorine Chemistry, 1990, XP002418739.
Langlois et al., "Fluorination of aromatic compounds by halogen exchange with fluoride anions ("Halex" reaction)", Journal of Fluorine Chemistry, 1996, XP000865520.
Synthesis, 1983, p. 904.

* cited by examiner

*Primary Examiner*—Kamal A Saeed
*Assistant Examiner*—Samantha L Shterengarts
(74) *Attorney, Agent, or Firm*—Baker Donelson Bearman, Caldwell & Berkowitz, PC

(57) ABSTRACT

The present invention relates to a novel process for preparing known 5-fluoro-1,3-dialkyl-1H-pyrazole-4-carbonyl fluorides which can be used as starting materials for active fungicidal ingredients by a halex reaction.

8 Claims, No Drawings

METHOD FOR THE PRODUCTION OF 5-FLUORO-1,3-DIALKYL-1H-PYRAZOL-4-CARBONYL FLUORIDES

CROSS REFERENCE TO RELATED APPLICATIONS

This is a 371 National Stage Application of International Application No. PCT/EP2006/008635 filed Sep. 5, 2006, which claims priority from German Application No. 10 2005 044 451.2.1 filed Sep. 17, 2005.

BACKGROUND OF THE INVENTION

1. Field of the Invention

The present invention relates to a novel process for preparing 5-fluoro-1,3-dialkyl-1H-pyrazole-4-carbonyl fluorides, a valuable intermediate for the preparation of fungicides, from the corresponding 5-chloro-1,3-dialkyl-1H-pyrazole-4-carbonyl chlorides.

2. Description of Related Art

It is already known that 5-fluoro-1,3-dimethyl-1H-pyrazole-4-carbonyl fluoride is obtained by reacting 5-chloro-1,3-dimethyl-1H-pyrazole-4-carbonyl chloride with potassium fluoride in the presence of a diluent, preferably sulpholane (cf. EP-A 0 776 889). One disadvantage of this process is the low space-time yield, as a result of which the process can be realized only with difficulty on the industrial scale. Secondly, the sulpholane can be removed from the product by distillation only with difficulty. In view of these limitations and disadvantages, there is a need for an improved process for the preparation of 5-fluoro-1,3-dialkyl-1H-pyrazole-4-carbonyl fluorides, by means of which the disadvantages intrinsic to the known processes, in particular high reaction temperatures and long reaction times, are avoided, and the desired fluorides are additionally obtained in good to very good yield at low reaction temperatures and relative short reaction times.

It is known that the halex reaction can sometimes be improved by addition of phase transfer-catalysts (PTC). The phase transfer catalysts used to date have been quaternary alkylammonium, alkylphosphonium, pyridinium, amidophosphonium, 2-azaallenium, carbophosphazenium and diphosphazenium salts (EP-A 1 266 904). The direct comparison of different catalysts shows that there are no general rules for the successful performance of a halex reaction. The fine adjustments with regard to solvent, solution, temperature, additives and process have to be performed individually for each substance (cf. J. Fluor. Chem. 2004, 125, 1031-1038).

It is also known that the water should be removed substantially from the reaction mixture for the success of the fluorination. For these purposes, azeotropic drying in the presence of toluene or chlorobenzene is utilized in production. This is particularly important in the case of fluorination of acid chlorides, in order to prevent the hydrolysis of the acid chloride group. The fluorination of 5-chloro-1,3-dialkyl-1H-pyrazole-4-carbonyl chlorides in polyethylene glycol dimethyl ether (PEG) with a boiling point of over 250° C. could be highly advantageous, since the product would be distillable directly out of the reaction mixture. Commercial PEGs contain typically different amounts water (typically 0.6 to 2%). In order to remove water, the PEG is dried azeotropically, so that the content of water (Karl Fischer) fell below 0.1%. The solvent was used for the fluorination of 5-chloro-1,3-dialkyl-1H-pyrazole-4-carbonyl chlorides (in-house results).

SUMMARY OF THE INVENTION

We have found that the fluorination of 5-chloro-1,3-dialkyl-1H-pyrazole-4-carbonyl chlorides in PEG with water content of below 0.1% with potassium fluoride at temperatures of 140° C. to 190° C. within 12 hours brought no success. The addition of conventional PTC such as quaternary alkylammonium, alkylphosphonium, pyridinium, amidophosphonium, 2-azaallenium, carbophosphazenium and diphosphazenium salts brought only slight improvement (30% yield).

It has now been found that 5-fluoro-1,3-dialkyl-1H-pyrazole-4-carbonyl fluorides of the formula (I)

in which $R^1$ and $R^2$ are each independently $C_1$-$C_3$-alkyl are obtained by converting 5-chloro-1,3-dialkyl-1H-pyrazole-4-carbonyl chlorides of the formula (II)

in which $R^1$ and $R^2$ are each as defined above, in the presence of potassium fluoride, in the presence of a phase transfer catalyst selected from (A) a quaternary phosphonium compound of the formula (III)

in which $R^3$, $R^4$, $R^5$ and $R^6$ are each independently $C_1$-$C_{22}$-alkyl, in each case optionally substituted aryl or ($C_1$-$C_4$-alkyl) aryl, where aryl is defined as phenyl or naphthyl, and the said substituents are halogen, $C_1$-$C_4$-alkyl, $C_1$-$C_4$-alkoxy, nitro or cyano, $X^-$ is an anion, or (B) an amidophosphonium salt of the formula (IV)

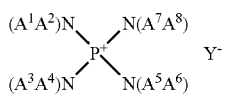

(IV)

in which

A$^1$, A$^2$, A$^3$, A$^4$, A$^5$, A$^6$, A$^7$ and A$^8$ are each independently C$_1$-C$_{12}$-alkyl or C$_2$-C$_{12}$-alkenyl, C$_4$-C$_8$-cycloalkyl, C$_6$-C$_{12}$-aryl, C$_7$-C$_{12}$-aralkyl, or A$^1$A$^2$, A$^3$A$^4$, A$^5$A$^6$ and A$^7$A$^8$ are each independently joined to one another directly or via O or N-A$^9$ to give a 3- to 7-membered ring, A$^9$ is C$_1$-C$_4$-alkyl, Y$^-$ is a monobasic acid radical or the equivalent of a polybasic acid radical, or (C) a compound of the formula (V)

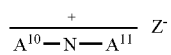

(V)

in which

A$^{10}$ and A$^{11}$ are each independently one of the following radicals

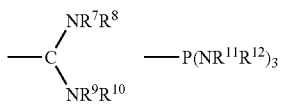

R$^7$, R$^8$, R$^9$, R$^{10}$, R$^{11}$ and R$^{12}$ are each independently C$_1$-C$_{10}$-alkyl C$_2$-C$_{10}$-alkenyl or C$_6$-C$_{12}$-aryl, or R$^7$R$^8$, R$^9$R$^{10}$, R$^{11}$R$^{12}$ are each independently joined directly to one another to give a 3- to 5-membered, saturated or unsaturated ring which contains one nitrogen atom and otherwise carbon atoms, where the radical

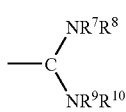

may also be a saturated or unsaturated, 4- to 8-membered ring which contains two nitrogen atoms and otherwise carbon atoms, Z$^-$ is an equivalent of an anion, or (D) a hexaalkylguanidinium salt of the formula (VI)

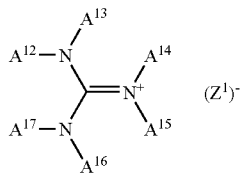

(VI)

in which

A$^{12}$, A1$^3$, A$^{14}$, A$^{15}$, A$^{16}$ and A$^{17}$ are each independently C$_1$-C$_{12}$-alkyl or C$_2$-C$_{12}$-alkenyl, C$_4$-C$_8$-cycloalkyl, C$_6$-C$_{12}$-aryl, C$_7$-C$_{12}$-aralkyl, or A$^{12}$A$^{13}$, A$^{14}$A$^{15}$ and A$^{16}$A$^{17}$ are each independently joined to one another directly or via O or N-A$^{18}$ to give a 3- to 7-membered ring, A$^{18}$ is C$_1$-C$_4$-alkyl, (Z$^1$)$^-$ is one equivalent of an anion, in the presence of a polyether of the formula (VII)

$$R^{13}—(O—C_mH_{2m})_r—OR^{14}$$ (VII)

in which

R$^{13}$ and R$^{14}$ are each independently C$_1$-C$_{16}$-alkyl, m is an integer from 2 to 6, r is an integer from 0 to 20, and in the presence of catalytic amounts of a protic compound from the group of sulpholane, dimethyl sulphoxide (DMSO), dimethylacetamide, dimethylformamide (DMF), N-methylpyrrolidone (NMP), 1,3-dimethylimidazolinone, HF, water, dichloromethane, chloroform, dichloroethane or trichloroethane; ketones such as acetone, butanone, methyl isobutyl ketone or cyclohexanone; nitriles such as acetonitrile, propionitrile, n- or i-butyronitrile; amides such as N,N-dimethylformamide, N,N-dimethylacetamide, N-methylformanilide, N-methylpyrrolidone or hexamethylphosphoramide, more preferably sulpholane, dimethyl sulphoxide, dimethylacetamide, NMP or water.

DETAILED DESCRIPTION OF A PREFERRED EMBODIMENT

Surprisingly, the 5-fluoro-1,3-dialkyl-1H-pyrazole-4-carbonyl fluorides of the formula (I) can be prepared under the inventive conditions with good yields in high purity and selectivity. A further advantage of the process according to the invention is that the reaction takes place even at 140-150° C. and that the product, after the fluorination, can be distilled directly out of the reaction mixture in pure form. In this case, the removal of the product from solvent is dispensed with completely. It is suspected that the addition of catalytic amounts of a protic compound such as sulpholane, DMF or water, under reaction conditions in the presence of KF (strong base), forms small amounts of HF, which greatly accelerates the reaction (first stage is the formation of 5-chloro-1,3-dialkyl-1H-pyrazole-4-carbonyl fluoride).

When, for example, 5-chloro-1,3-dimethyl-1H-pyrazole-4-carbonyl chloride, potassium fluoride, tetraphenylphosphonium bromide, polyethylene glycol dimethyl ether 500 and 0.1% by weight of sulpholane are used as starting materials, the process according to the invention can be illustrated in detail by the following formula scheme:

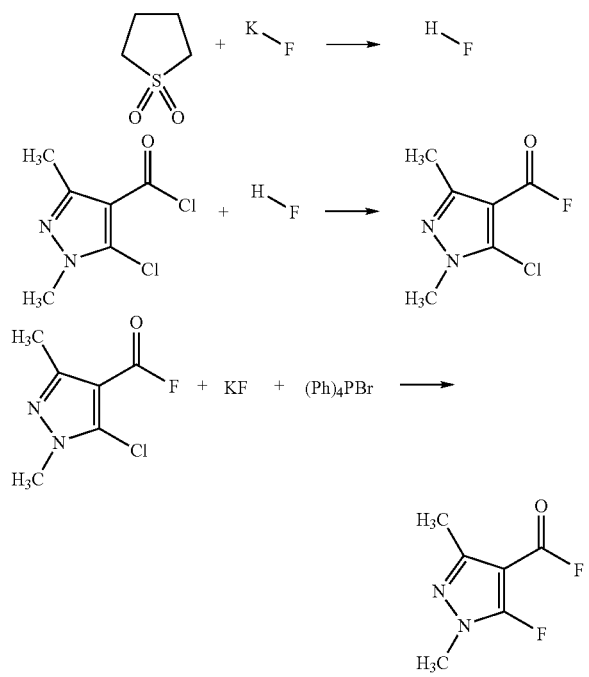

The 5-chloro-1,3-dialkyl-1H-pyrazole-4-carbonyl chlorides used as starting materials in the performance of the process according to the invention are defined generally by the formula (TI). In this formula (II), the $R^1$ and $R^2$ radicals are each independently preferably methyl, ethyl, n-propyl or isopropyl, more preferably simultaneously methyl.

5-Chloro-1,3-dialkyl-1H-pyrazole-4-carbonyl chlorides of the formula (II) are known or can be prepared by known processes (cf. EP-A 0 776 889).

The potassium fluoride also required as a starting material is a known synthesis chemical.

The quaternary phosphonium compounds usable as phase transfer catalysts in the performance of the process according to the invention are defined generally by the formula (III). In this formula (III), $R^3$, $R^4$, $R^5$ and $R^6$ are each independently preferably $C_1$-$C_{18}$-alkyl, phenyl or naphthyl each optionally substituted by fluorine, chlorine, bromine, methyl, methoxy, nitro or cyano, more preferably each butyl, octyl, hexadecyl, octadecyl or phenyl. $X^-$ is preferably an anion, where X is selected from the group of F, $HF_2$, Cl, I, Br, $BF_4$, ½ $SO_4^{2-}$, benzenesulphonyl, p-toluenesulphonyl, $HSO_4$, $PF_6$ or $CF_3SO_3$. Very particular preference is given to the following phosphonium compounds of the formula (III): hexadecyltributyl phosphonium bromide, stearyltributyl phosphonium bromide, tetrabutylphosphonium chloride, tetrabutyl phosphonium bromide, tetraoctyl phosphonium bromide, tetraphenyl phosphonium chloride or tetraphenyl phosphonium bromide.

Phosphonium compounds of the formula (III) are known (cf. WO 98/32532).

The amidophosphonium salts likewise usable as phase transfer catalysts in the performance of the process according to the invention are defined generally by the formula (IV). In this formula (IV), $A^1$, $A^2$, $A^3$, $A^4$, $A^5$, $A^6$, $A^7$ and $A^8$ are each independently preferably $C_1$-$C_8$-alkyl, $C_2$-$C_8$-alkenyl, $C_5$-$C_6$-cycloalkyl, more preferably $C_1$-$C_4$-alkyl. Examples of alkyl include methyl, ethyl, n-propyl, i-propyl, n-butyl, i-butyl, n-pentyl, 3-methylbutyl, n-hexyl, 2-ethylhexyl, in particular methyl, ethyl, n-propyl, n-butyl, and examples of alkenyl include allyl, prop-(2)-enyl, n-but-(2)-enyl, and examples of cycloalkyl include cyclopentyl, cyclohexyl, 4-methylcyclohexyl, 4-tert-butylcyclohexyl. It is also possible to use a compound of the formula (IV) in which $A^1A^2$, or $A^1A^2$ and $A^3A^4$, or $A^1A^2$ and $A^3A^4$ and $A^5A^6$, or $A^1A^2$ and $A^3A^4$ and $A^5A^6$ and $A^7A^8$, are joined to one another directly or via O or N-$A^9$ to give a saturated or unsaturated ring having 5 or 6 ring members. Accordingly, these compounds contain one, two, three or four of the aforementioned rings. It is also possible to use a compound of the formula (IV) in which $A^1A^2$, or $A^1A^2$ and $A^3A^4$, or $A^1A^2$ and $A^3A^4$ and $A^5A^6$, or $A^1A^2$ and $A^3A^4$ and $A^5A^6$ and $A^7A^8$, are joined together to form a ring which includes the nitrogen atom on which the particular $A^1$ to $A^8$ radicals reside, if appropriate O— or N-$A^9$ and $CH_2$ groups as ring members. In this substance group, the nitrogen atom with the $A^1$ to $A^8$ radicals present thereon in each case form, for example, a hexahydropyridine ring, tetrahydropyrrole ring, a hexahydropyrazine ring or morpholine ring. Accordingly, these compounds contain one, two, three or four of the aforementioned rings. $A^9$ is preferably methyl, ethyl, n-propyl, i-propyl, n-butyl, i-butyl, sec-butyl or tert-butyl.

In the compound of the formula (IV), $Y^-$ is a monobasic acid radical or the equivalent of a polybasic acid radical, in particular the radical of an inorganic mineral acid, of an organic carboxylic acid, of an aliphatic or aromatic sulphonic acid. Typically, a compound of the formula (IV) is used in which Y is F, Cl, Br, S, $HF_2$, $BF_4$, benzenesulphonyl, p-toluenesulphonyl, $HSO_4$, $PF_6$, $CF_3SO_3$, in particular F, Cl, Br, S, $HF_2$, $BF_4$, is used. Examples of compounds of the formula (IV) include: tetrakis(dimethylamino)phosphonium chloride, tetrakis(diethylamino)phosphonium chloride, tetrakis(dimethylamino)phosphonium bromide, tetrakis(diethylamino)phosphonium bromide, tetrakis(dipropylmino) phosphonium chloride or bromide, tris(diethylamino) (dimethylamino)phosphonium chloride or bromide, tetrakis (dibutylamino)phosphonium chloride or bromide, tris (dimethylamino)-(diethylamino)phosphonium chloride or bromide, tris(dimethylamino)(cyclopentylamino)phosphonium chloride or bromide, tris(dimethylamino)(dipropylamino)phosphonium chloride or bromide, tris(dimethylamino) (dibutylamino)phosphonium chloride or bromide, tris (dimethylamino)(cyclo-hexylamino)phosphonium chloride or bromide, tris(dimethylamino)(diallylamino)phosphonium chloride or bromide, tris(dimethylamino)(dihexylamino) phosphonium chloride or bromide, tris-(diethylamino)(dihexylamino)phosphonium chloride or bromide, tris(dimethylamino)(diheptylamino)phosphonium chloride or bromide, tris(diethylamino)-(diheptylamino)phosphonium chloride or bromide, tetrakis(pyrrolidino)phosphonium chloride or bromide, tetrakis(piperidino)phosphonium chloride or bromide, tetrakis(morpholino)phosphonium chloride or bromide, tris (piperidino)(diallylamino)phosphonium chloride or bromide, tris(pyrrolidino)(ethylmethylamino)phosphonium chloride or bromide, tris(pyrrolidino)(diethylamino)phosphonium chloride or bromide.

Amidophosphonium salts of the formula (IV) are known (cf WO 98/32532).

The compounds likewise usable as phase transfer catalysts in the performance of the process according to the invention are defined generally by the formula (V). In this formula (V), $R^7$, $R^8$, $R^9$, $R^{10}$, $R^{11}$ and $R^{12}$ are each independently preferably methyl, ethyl, n-propyl, isopropyl, n-, iso-, sec- or tert-butyl. $R^7$ and $R^8$, $R^9$ and $R^{10}$, $R^{11}$ and $R^{12}$ are preferably identical. In the formula (V), $Z^-$ is preferably an equivalent of an anion, where Z is selected from Cl, Br, $(CH_3)_3SiF_2$, $HF_2$, $H_2F_2$, $BF_4$, $PF_6$, carbonate or sulphate.

Particularly preferred compounds of the formula (V) are illustrated by the following formulae (V-1) to (V-3):

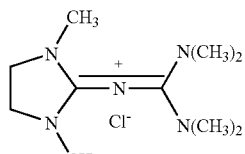

(V-1)

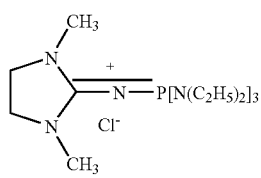

(V-2)

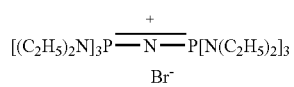

(V-3)

The compounds of the formula (V) are known (cf. EP-A 1 266 904).

The hexaalkylguanidinium salts likewise usable as phase transfer catalysts in the performance of the process according to the invention are defined generally by the formula (VI). In this formula (VI), $A^{12}$, $A^{13}$, $A^{14}$, $A^{15}$, $A^{16}$ and $A^{17}$ are each independently preferably $C_1$-$C_8$-alkyl, $C_2$-$C_8$-alkenyl, $C_5$-$C_6$-cycloalkyl, more preferably $C_1$-$C_4$-alkyl. Examples of alkyl include methyl, ethyl, n-propyl, i-propyl, n-butyl, i-butyl, n-pentyl, 3-methylbutyl, n-hexyl, 2-ethylhexyl, in particular methyl, ethyl, n-propyl, n-butyl, and examples of alkenyl include allyl, prop-(2)-enyl, n-but-(2)-enyl, and examples of cycloalkyl include cyclopentyl, cyclohexyl, 4-methylcyclohexyl, 4-tert-butylcyclohexyl. It is also possible to use a compound of the formula (VI) in which $A^{12}A^{13}$, or $A^{12}A^{13}$ and $A^{14}A^{15}$, or $A^{12}A^{13}$ and $A^{14}A^{15}$ and $A^{16}A^{17}$, are joined together directly or via O or N-$A^{18}$ to give a saturated or unsaturated ring having 5 or 6 ring members. Accordingly, these compounds contain one, two or three of the aforementioned rings. It is also possible to use a compound of the formula (VI) in which $A^{12}A^{13}$, or $A^{12}A^{13}$ and $A^{14}A^{15}$, or $A^{12}A^{13}$ and $A^{14}A^{15}$ and $A^{16}A^{17}$, are joined to form a ring which includes the nitrogen atoms on which the particular $A^1$ to $A^8$ radicals reside, if appropriate O or N-A 18 and $CH_2$ groups as ring members. In this substance group, the nitrogen atom with the $A^{12}$ to $A^{17}$ radicals present thereon forms, for example, a hexahydropyridine ring, tetrahydropyrrole ring, a hexahydropyrazine ring or morpholine ring. Accordingly, these compounds contain one, two or three of the aforementioned rings. $A^{18}$ is preferably methyl, ethyl, n-propyl, i-propyl, n-butyl, i-butyl, sec-butyl or tert-butyl. In the formula (VI), $(Z^1)^-$ is an equivalent of an anion, where $Z^1$ is selected from Cl, Br, $(CH_3)_3SiF_2$, $HF_2$, $H_2F_2$, $BF_4$, $PF_6$, carbonate or sulphate.

Hexaalkyguanidinium salts of the formula (VI) are known (Synthesis, 1983, 904, U.S. Pat. No. 5,082,968).

The polyethers also required as starting materials in the performance of the process according to the invention are defined generally by the formula (VII). In this formula (VII), $R^{13}$ and $R^{14}$ are preferably each $C_1$-$C_8$-alkyl; m is preferably 2 or 3; r is preferably an integer of 1 to 18, in particular of 4 to 14. Preferred polyethers of the formula (VII) have a mean molar mass between 300 and 800 g/mol. Particular preference is given to a mixture of polyethylene glycol dimethyl ethers of chain lengths r from 6 to 17 and a mean molar mass of 500 g/mol.

Polyethers of the formula (VII) are known (cf. WO 98/32532).

According to the invention, the phase transfer catalyst used may be any conceivable combination of a compound of the formula (III) as per (A) with a compound of the formula (IV) as per (B) or with a compound of the formula (V) as per (C) or with a mixture of (B) and (C), where the compounds mentioned as per (A), (B) and (C) themselves may each likewise be a mixture of corresponding compounds. Likewise conceivable are all possible combinations with a polyether of the formula (VII).

The reaction temperatures in the performance of the process according to the invention may be varied within a relatively wide range. In general, working temperatures are 120° C. to 150° C., preferably 130° C. to 150° C.

In the performance of the process according to the invention, generally between 0.5 and 3 mol %, preferably 1-3 mol %, of catalyst A, B, C or D, and 2 to 2.5 mol, preferably 2.1 mol, of KF are used per mole of 5-chloro-1,3-dialkyl-1H-pyrazole-4-carbonyl chloride of the formula (II).

The amount of polyethylene glycol ether is 0.25 to 2 g, preferably 0.5 to 1 g, per gram of 5-chloro-1,3-dialkyl-1H-pyrazole-4-carbonyl chloride of the formula (II). The amount of protic additive such as sulpholane, NMP, water, etc is 0.01 to 0.1 g per gram of 5-chloro-1,3-dialkyl-1H-pyrazole-4-carbonyl chloride of the formula (II).

Depending on the reactivity of the reactants, the reaction time may be up to 10 hours, but the reaction may also be terminated at full conversion at an even earlier stage. Preference is given to reaction times of 3-5 hours.

All processes according to the invention are generally carried out under standard pressure. However, it is also possible to work under elevated or reduced pressure, generally between 0.1 bar and 10 bar.

The 5-fluoro-1,3-dialkyl-1H-pyrazole-4-carbonyl fluorides of the formula (I) preparable by the process according to the invention are valuable intermediates for the preparation of fungicides (cf., for example, EP-A 0 776 889).

The inventive preparation of 5-fluoro-1,3-dialkyl-1H-pyrazole-4-carbonyl fluorides of the formula (I) is described in the examples below, which further illustrate the above description. However, the examples are not to be interpreted in a restrictive manner.

PREPARATION EXAMPLES

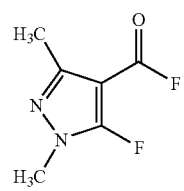

Example 1

Under argon, 19.3 g (100 mmol) of 5-chloro-1,3-dimethyl-1H-pyrazole-4-carbonyl chloride are initially charged in polyethylene glycol dimethyl ether (KF water content 0.05%). 17.43 g (300 mmol) of potassium fluoride, 0.50 g (2 mmol) of bis(dimethylamino)[(1,3-dimethyl-imidazolidin-2-ylidene)amino]methylium chloride and 100 mg of water are then added, and the mixture is heated to 150° C. and stirred at this temperature for a further 5 hours. Subsequently, the product was distilled off under reduced pressure. 13 g (82% of theory) of 5-fluoro-1,3-dimethyl-1H-pyrazole-4-carbonyl fluoride are obtained. m.p. 85-87° C. at 10 mbar.

Example 2

Under argon, 19.3 g (100 mmol) of 5-chloro-1,3-dimethyl-1H-pyrazole-4-carbonyl chloride are initially charged in polyethylene glycol dimethyl ether (KF water content 0.05%). 17.43 g (300 mmol) of potassium fluoride, 1 g of tetraphenylphosphonium bromide and 300 mg of sulpholane are then added, and the mixture is heated to 150° C. and stirred at this temperature for a further 5 hours. Subsequently, the product was distilled off under reduced pressure. 13.3 g (83% of theory) of 5-fluoro-1,3-dimethyl-1H-pyrazole-4-carbonyl fluoride are obtained. Melting point 85-87° C. at 10 mbar.

The invention claimed is:
1. Process for preparing 5-fluoro-1,3-dialkyl-1H-pyrazole-4-carbonyl fluorides of the formula (I)

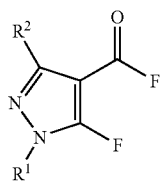

(I)

in which $R^1$ and $R^2$ are each independently $C_1$-$C_3$-alkyl, comprising: converting
5-chloro-1,3-dialkyl-1H-pyrazole-4-carbonyl chlorides of the formula (II)

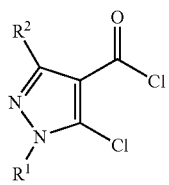

(II)

in which $R^1$ and $R^2$ are each as defined above
in the presence of potassium fluoride,
in the presence of a phase transfer catalyst selected from
(A) a quaternary phosphonium compound of the formula (III)

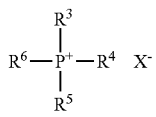

(III)

in which
$R^3$, $R^4$, $R^5$ and $R^6$ are each independently $C_1$-$C_{22}$-alkyl, in each case optionally substituted aryl or ($C_1$-$C_4$-alkyl)aryl, where aryl is defined as phenyl or naphthyl, and the said substituents are halogen, $C_1$-$C_4$-alkyl, $C_1$-$C_4$-alkoxy, nitro or cyano,
$X^-$ is an anion,
or
(B) an amidophosphonium salt of the formula (IV)

(IV)

in which
$A^1$, $A^2$, $A^3$, $A^4$, $A^5$, $A^6$, $A^7$ and $A^8$ are each independently $C_1$-$C_{12}$-alkyl or $C_2$-$C_{12}$-alkenyl, $C_4$-$C_8$-cycloalkyl, $C_6$-$C_{12}$-aryl, $C_7$-$C_{12}$-aralkyl, or
$A^1A^2$, $A^3A^4$, $A^5A^6$ and $A^7A^8$ are each independently joined to one another directly or via O or N-$A^9$ to give a 3- to 7-membered ring,
$A^9$ is $C_1$-$C_4$-alkyl,
$Y^-$ is a monobasic acid radical or the equivalent of a polybasic acid radical,
or
(C) a compound of the formula (V)

(V)

in which
$A^{10}$ and $A^{11}$ are each independently one of the following radicals

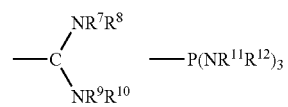

$R^7$, $R^8$, $R^9$, $R^{10}$, $R^{11}$ and $R^{12}$ are each independently $C_1$-$C_{10}$-alkyl, $C_2$-$C_{10}$-alkenyl or $C_6$-$C_{12}$-aryl, or
$R^7R^6$, $R^9R^{10}$, $R^{11}R^{12}$ are each independently joined directly to one another to give a 3- to 5-membered, saturated or unsaturated ring which contains one nitrogen atom and otherwise carbon atoms,
where the radical

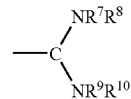

may also be a saturated or unsaturated, 4- to 8-membered ring which contains two nitrogen atoms and otherwise carbon atoms, $Z^-$ is an equivalent of an anion,
or
(D) a hexaalkylguanidinium salt of the formula (VI)

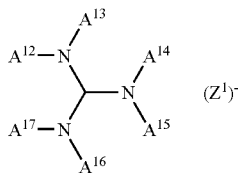

in which
$A^{12}, A^{13}, A^{14}, A^{15}, A^{16}$ and $A^{17}$ are each independently $C_1$-$C_{12}$-alkyl or $C_2$-$C_{12}$-alkenyl, $C_4$-$C_8$-cycloalkyl, $C_6$-$C_{12}$-aryl, $C_7$-$C_{12}$-aralkyl, or
$A^{12}A^{13}$, $A^{14}A^{16}$ and $A^{16}A^{17}$ are each independently joined to one another directly or via O or N-$A^{18}$ to give a 3- to 7-membered ring,
$A^{18}$ is $C_1$-$C_4$-alkyl,
$(Z^1)^-$ is one equivalent of an anion,
in the presence of a polyether of the formula (VII)

 (VII)

in which
$R^{13}$ and $R^{14}$ are each independently $C_1$-$C_{16}$-alkyl,
m is an integer from 2 to 6,
r is an integer from 0 to 20,
and in the presence of catalytic amounts of a protic compound selected from the group consisting of sulpholane, dimethyl sulphoxide (DMSO), dimethylacetamide, dimethylformamide (DMF), N-methylpyrrolidone (NMP), 1,3-dimethylimidazolinone, HF, water, dichloromethane, chloroform, dichloroethane, trichloroethane, ketones nitriles, and amides.

2. Process according to claim 1, wherein 5-chloro-1,3-dimethyl-1H-pyrazole-4-carbonyl chloride is used as the starting material of the formula (II).

3. Process according to claim 1, wherein a quaternary phosphonium compound of the formula (III) is selected from the group consisting of hexadecyltributylphosphonium bromide, stearyltributylphosphonium bromide, tetrabutylphosphonium chloride, tetrabutylphosphonium bromide, tetraoctylphosphonium bromide, tetraphenylphosphonium chloride and tetraphenylphosphonium bromide.

4. Process according to claim 1, wherein an amidophosphonium salt of the formula (IV) is selected from the group consisting of: tetrakis(dimethylamino)phosphonium chloride, tetrakis(diethylamino)phosphonium chloride, tetrakis(dimethylamino)phosphonium bromide, tetrakis(diethylamino)phosphonium bromide, tetrakis(dipropylamino) phosphonium chloride or bromide, tris(diethylamino) (dimethylamino)phosphonium chloride or bromide, tetrakis(dibutylamino)phosphonium chloride or bromide, tris (dimethylamino)(diethylamino)phosphonium chloride or bromide, tris(dimethylamino)(cyclopentylamino)phosphonium chloride or bromide, tris(dimethylamino)(dipropylamino)phosphonium chloride or bromide tris(dimethylamino) (dibutylamino)phosphonium chloride or bromide, tris (dimethylamino)(cyclohexylamino)phosphonium chloride or bromide, tris(dimethylamino)(diallylamino)phosphonium chloride or bromide, tris(dimethylamino)(dihexylamino) phosphonium chloride or bromide, tris(diethylamino)(dihexylamino)phosphonium chloride or bromide, tris(dimethylamino)(diheptylamino)phosphonium chloride or bromide, tris(diethylamino)(diheptylamino)phosphonium chloride or bromide, tetrakis(pyrrolidino)phosphonium chloride or bromide, tetrakis(piperidino)phosphonium chloride or bromide, tetrakis(morpholino)phosphonium chloride or bromide, tris (piperidino)(diallylamino)phosphonium chloride or bromide, tris(pyrrolidino)(ethylmethylamino)phosphonium chloride or bromide, and tris(pyrrolidino)(diethylamino) phosphonium chloride or bromide.

5. Process according to claim 1, wherein a compound of the formula (V) is selected from the group consisting of:

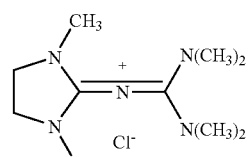 (V-1)

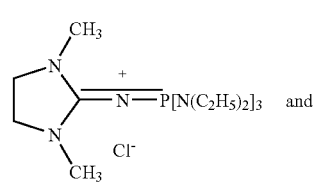 (V-2)

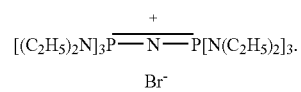 (V-3)

6. Process according to claim 1, wherein hexaalkylguanidinium salt of the formula (VI) comprises a compound wherein $A^{12}$, $A^{13}$, $A^{14}$, $A^{15}$, $A^{16}$ and $A^{17}$ are each independently $C_1$-$C_8$-alkyl, $C_2$-$C_8$-alkenyl, $C_5$-$C_6$-cycloalkyl; or in which $A^{12}A^{13}$, or $A^{12}A^{13}$ and $A^{14}A^{16}$, or $A^{12}A^{13}$ and $A^{14}A^{15}$ and $A^{16}A^{17}$, are joined to one another directly or via O or N-$A^{18}$ to give a saturated or unsaturated ring having 5 or 6 ring members, and $A^{18}$ is methyl, ethyl, n-propyl, i-propyl, n-butyl, i-butyl, sec-butyl or tert-butyl, and $(Z^1)^-$ is selected from Cl, Br, $(CH_3)_3SiF_2$, $HF_2$, $H_2F_2$, $BF_4$, $PF_6$, carbonate or sulphate.

7. Process according to claim 1, wherein the polyether of the formula (VII) comprises a compound wherein $R^{13}$ and $R^{14}$ are each $C_1$-$C_8$-alkyl, m is 2 or 3 and r is an integer from 1 to 18.

8. Process according to claim 1, wherein the phase transfer catalyst is selected from the group consisting of
(A) tetraphenylphosphonium bromide
and
(C) bis(dimethylamino)[(1,3-dimethylimidazolidin-2-ylidene)amino]methylium chloride is converted in the presence of polyethylene glycol dimethyl ether
and said process is conducted in the presence of a catalytic amount of sulpholane.

* * * * *